(12) United States Patent
Zisapel et al.

(10) Patent No.: US 7,355,054 B2
(45) Date of Patent: *Apr. 8, 2008

(54) INDOLE DERIVATIVES

(75) Inventors: Nava Zisapel, Tel Aviv (IL); Moshe Laudon, Kfar Saba (IL)

(73) Assignee: Neurim Pharmaceuticals (1991) Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/032,057

(22) Filed: Jan. 11, 2005

(65) Prior Publication Data

US 2005/0159463 A1    Jul. 21, 2005

Related U.S. Application Data

(62) Division of application No. 09/979,658, filed as application No. PCT/IL00/00295 on May 24, 2000, now Pat. No. 6,858,642.

(30) Foreign Application Priority Data

May 27, 1999   (IL) ...................................... 130169

(51) Int. Cl.
*A61K 31/404*   (2006.01)
*C07D 407/12*   (2006.01)

(52) U.S. Cl. ...................... 548/467; 548/504; 548/510; 514/414; 424/401

(58) Field of Classification Search ................ 548/467, 548/504, 510

See application file for complete search history.

(56) References Cited

U.S. PATENT DOCUMENTS 5,624,935 A    4/1997  Fujita et al.
5,756,507 A    5/1998  Goulet et al.
6,858,642 B1 *  2/2005  Zisapel et al. .............. 514/419

FOREIGN PATENT DOCUMENTS

| JP | 9-227369 | 9/1997 |
| WO | WO 92/07829 A1 | 5/1992 |
| WO | WO 97/23202 | 7/1997 |
| WO | WO-99/11619 A1 * | 3/1999 |

OTHER PUBLICATIONS

Mo et al., CA 130:3741, 1998.*
Knoch et al., CA 117:88914, 1992.*
Chem. Abstr., vol. 105, No. 19. Abstract No. 164474v, Grin, L.M. et al., "Synthesis and hypoglycemic activity of N-acyl-substituted 5-methoxytryptamine." Nov. 10, 1986.
Chem. Abstr., vol. 73, No. 17. Abstract No. 87785p, Yamamoto, H et al., "Novel cinnamates" Chem., Oct. 26, 1970.
Solomina et al., Mrmjanskij Khimicheskii Zhurnal, 1979, 32(12) 956-961.
Somei et al., "Syntheses of 1-Hydroxytryptamines and Serotonins having Fattyactyl or (E)-3-phenylpropenoyl Derivatives as a Nb-Substituent, and a Novel Homologation on the 3-Substituent of the 1-Hydroxytryptamines upon Treatment with Diazomethane," *Heterocycles*, Jun. 1, 1998, vol. 48, No. 6, pp. 1117-1120.
Somet et al., Heterocycles, 1998, 48(6), 1117-1120.
Wang et al., Chem. Pharm. Bull, 1997, 45(4) 715-718.

* cited by examiner

*Primary Examiner*—Laura L. Stockton
(74) *Attorney, Agent, or Firm*—Rothwell, Figg, Ernst & Manbeck

(57) ABSTRACT

The invention relates to $1\text{-}(R^1)\text{-}2\text{-}(R^2)\text{-}3\text{-}(Y\text{---}X\text{---}NH\text{-}A\text{-}$ or $Z\text{-}A\text{-})\text{-}4,5,6,7\text{-}R)_{0\text{-}4}$-indoles, and their acid addition salts where the compounds are basic, wherein A is $C_{1\text{-}4}$ alkylene, X is $>CH_2$, $>C=O$ or $>C=S$, and the other symbols have various defined values, and to pharmaceutical, skin-protective and cosmetic compositions which comprise them.

17 Claims, No Drawings

INDOLE DERIVATIVES

FIELD AND BACKGROUND OF THE INVENTION

The present invention relates to new compounds which are derivatives of indole, pharmaceutical formulations containing them, and use of the compounds in the manufacture of medicaments for treating various diseases.

The novel compounds described herein are structurally and functionally related to melatonin, 3-(2-acetaminoethyl)-5-methoxyindole, a hormone produced primarily by the pineal gland. Melatonin is the principal hormone secreted by the pineal gland in all vertebrates. In all mammals studied to date, including humans, a nocturnal rise in the production of melatonin by the pineal gland is evident, melatonin production by the body is acutely suppressed by light. Melatonin is involved in the coordination of photoperiod dependent and physiological processes. The ability of the animals or humans to respond to the melatonin signal may depend upon melatonin receptors. Melatonin acts on the CNS to affect neural mechanisms through receptors located in the brain. Additionally, a number of studies indicate the existence of direct effects of melatonin in peripheral organs via peripheral melatonin receptors. Melatonin receptors are present in the heart, lungs, prostate gland, gonads, white blood cells, retina, pituitary, thyroid, kidney, gut and blood vessels. Retention patterns of radioactive-melatonin injected to rats demonstrate melatonin accumulation in the brain, pituitary, lung, heart, gonads and accessory sex organs (Withyachumnarnkul et al., Life Sci, 12:1757-65, 1986).

The synthesis and secretion of melatonin exhibit a circadian rhythm that changes with the seasons and with age, e.g., pubescence and senescence. There is very strong evidence that melatonin is important for the regulation of a variety of neural and endocrine functions, especially those that exhibit circadian and circannual rhythmicity.

Melatonin has been implicated in many human disorders. Some are known to be linked to chronobiological abnormalities. Melatonin has been administered to re-synchronize circadian rhythms that are out of phase with the local photoperiodical cycle. For example, sleep/wake disorders with rapid crossing of time zones (jet lag), or in delayed sleep phase syndrome (DSPS) patients, changes in work shifts, or those experienced by blind people can be treated with melatonin or melatonin analogs (see U.S. Pat. Nos. 4,600,723 and 4,666,086 of Short et al. and U.S. Pat. No. 5,242,941 of Lewy et al.). However, it appears that melatonin also has direct sedative/hypnotic properties in normal human subjects (e.g., Waldhauser et al., Psychopharmacology, 100: 222-226, 1990; Vollrath et al., Bioscience, 29:327-329, 1981; Dollins et al., Proc. Natl Acad. Sci, 99:1824-1828, 1994; U.S. Pat. No. 5,403,851 of D'Orlando et al). Three melatonin receptor subtypes have been identified so far mt-1, MT-2 and Me11c (Barrett et al., Biol. Signals Recept., 1999, 8: 6-14). MT-2 is localized mainly in the central nervous system and mt-1, is localized in the CNS as well as in peripheral organs such as kidney and the urogenital tract (Dubocovich et al., IUPHAR media, London, UK, 187-93, 1998). The presently known subtypes are not sufficient to evaluate the large variety of melatonin effects and additional receptor subtypes await discovery.

Melatonin has been demonstrated in a number of rodent experimental paradigms to have both anxiolytic (Golus and King, Pharmacol. Biochem. Behav., 41:405-408, 1992, Naranjo-Rodriguez et al., Soc. Neurosci. Abst., 18:1167, 1992; Golombek et al., Eur. J. Pharmacol, 237:231-236, 1993) and antiseizure activity (Brallowsky, Electroencephalo. Clin. Neurophysiol., 41:314-319, 1976; Fariello et al., Neurology, 27:567-570, 1977; Rudeen et al., Epilepsia, 21:149-154, 1980; Sugden, J. Pharmacol Exp. Ther., 227: 587-591, 1983; Golombek et al., Eur. J. Pharmacol, 210: 253-258, 1992).

Melatonin is effective in the treatment of cluster headache and migraine (Claustrat et al., Headache, 29:241-4, 1989). Melatonin may play a role in other psychiatric conditions, particularly depression, but also mania and schizophrenia (see Dobocovich, "Antidepressant Agents"; U.S. Pat. No. 5,093,352; Miles and Philbrick, Biol. Psychiatry, 23:405-425, 1988; Sandyk and Kay, Schizophr. Bull., 16:653-662, 1990). In some instance, psychiatric disorders may have underlying chronobiological etiologies (e.g. seasonal effective disorder) and are definite candidates for melatonin therapy.

Melatonin is involved in the regulation of circadian and circannual changes in body temperature. Administration of exogenous melatonin to humans lowers core body temperature (Strassman et al., J. Appl. Physiol, 71:2178-2182, 1991; Cagnacci et al., J. Clin. Endocrinol. Merab., 75:447-452, 1992). Melatonin may also possess analgesic properties (Sugden, J. Pharmacol. Exp. Ther., 227:587-591, 1983). Therefore, melatonin-like compounds may be useful as an alternative to non-steroidal anti-inflammatory, anti-pyretic drugs, such as aspirin, acetaminophen and ibuprofen.

It is known that melatonin levels decrease with advancing age (Sack et al., J. Pineal Res., 4:379-388, 1986; Waldhauser et al., J. Clin. Endocrinol. Metab., 66:648-652, 1988; Van Coavorden et al., Am. J. Physiol., 260:E651-661, 1991) which may contribute to some disorders. Neurodegenerative diseases often associated with aging, such as Alzheimer's and Parkinson's diseases, may be treated with melatoninergic compounds (Maurizi, Med. Hypotheses, 31:233-242, 1990; Sandyk, Int. J. Neurosci., 50:37-53, 1990; Skene et al., Brain Rev., 528:170-174, 1990).

Sleep disorders in the elderly have been shown to respond to melatonin treatment (Garfinkel et al., Lancet, 346:541-543, 1995; U.S. Pat. No. 5,498,423 of Zisapel). Soporific effects of melatonin (0.3-240 mg) have been reported in humans following intravenous, intranasal and oral administration. Apart from its soporific effects, exogenous melatonin may affect sleep via its phase-resetting action on the biological clock. Melatonin administration advanced sleep in delayed sleep syndrome patients, and synchronized sleep to the day-night cycles in blind subjects. The efficacy of melatonin (0.3-5 mg/os) for treatment of insomnia has been demonstrated in studies performed mainly with elderly patients, patients treated with atenolol and chronic heart patients, most of which patients have low or distorted melatonin rhythms. In some of these studies, formulations which release melatonin throughout the night were used, in order to circumvent fast clearance of the hormone and to mimic its endogenous profile (Nutrition, 1998, 14: 1-2. The Aging Male, 1998, 1: 1-8). Melatonin, 3 mg, given to patients with sleep disorders and dementia for 21 days, significantly augmented sleep quality and decreased the number of wakening episodes, while agitated behavior at night (sundowning) decreased significantly (Biol. Signals Recept., 1999, 8(1-2): 126-31).

We have recently found that melatonin treatment may be beneficial not only for improving sleep quality, but may also lead to an improvement in the general state of diabetic patients, as indicated by the decrease in HbA1c levels after long-term treatment.

Daily melatonin supplementation to male Sprague-Dawley rats, starting at middle age (10 months) and continuing into old age (22 months) via the drinking water at a dosage of 4 μg/ml, restored the age-related elevated levels of relative (% of body weight) retroperitoneal and epididymal fat, as well as plasma insulin and leptin levels to youthful (4 month) levels (Rasmussen et al., Endocrinology, 1999, 140 (2): 1009-12).

Even osteoporosis may have a melatoninergic component (Sandyk et al., Int. J. Neurosci., 62:215-225, 1992). In fact, melatonin has been suggested to be an anti-aging, anti-stress hormone (Armstrong and Redman, Med. Hypotheses, 34:300-309, 1991; Reiter, Bioassays, 14:169-175, 1992). This may be due to its action as a free radical scavenger (Pooggeler et al., J. Pineal Res., 14:151-168, 1993) or its interaction with the immune system (Maestroni and Conti, J. Neuroimmun., 28:167-176 1990; Fraschini et al., Acta. Oncol., 29:775-776 1990; Guerrero and Reiter, Endocr. Res., 18:91-113, 1992). Melatonin may protect from ischemic stroke (Cho et al., Brain Research, 755:335-338, 1997), decrease cell-death in Alzheimer's disease (Pappola et al., J Neurosci, 17:1685-90, 1997) and lower the risk of SIDS in young infants with low endogenous melatonin levels (Israel Patents Nos. 115861/2 and U.S. Pat. No. 5,500,225 of Laudon et al).

Related to the above are the findings that melatonin has oncostatic properties in a variety of cancers, the most studied being its effect on estrogen receptor positive breast cancers (Blasak and Hill, J. Neural. Transm. Suppl., 21:433-449, 1986; Gonzalez et al., Melanoma. Res., 1:237-243, 1991; Lissoni et al., Eur. J. Cancer, 29A:185-189, 1993; Shellard et al., Br. J. Cancer, 60:288-290, 1989; Philo and Berkowitz, J. Urol., 139:1099-1102, 1988; see U.S. Pat. No. 5,196,435 of Clemens et al. and U.S. Pat. No. 5,272,141 of Fraschini et al.). It is also possible that melatonin has antiproliferative effects on noncancerous cells as well and may be of use to treat benign tumors and proliferative diseases such as BPH (U.S. Pat. No. 5,750,557 and European Patent No. EP 0565296B of Zisapel) and Psoriasis.

A major portion of research on melatonin has been devoted to studying is effects on reproduction, particularly in seasonally breeding species (such as hamsters and sheep), in which Melatonin is known to regulate fertility and puberty, hibernation, and coat color. These effects have obvious significance for animal husbandry use. Reproductive endocrine uses in humans for melatonin include: contraceptive and fertility agents, treatment for precocious puberty, treatment for premenstrual syndrome and hyperprolactinemia (Pevre et al., J. Clin. Endocrinol. Metab., 47:1383-1386, 1978; Purry et al., Am. J. Psychiatry, 144:762-766, 1987; Waldhauser et al., Clin. Endocrinol. Metab., 73:793-796, 1991; Bispink et al., Pineal Res., 8:97-106, 1990; Cagnacci et al., J. Clin. Endocrinol. Metab., 73:210-220, 1991; Voordouw et al., J. Clin. Endocrinol. Metab., 74:107-108, 1992; see U.S. Pat. Nos. 4,855,305 and 4,945,103 of Cohen et al., and U.S. Pat. No. 5,272,141 of Fraschini et al.). It is likely that melatonin compounds may also be useful in other endocrine conditions, particularly those involving growth hormone (Cramer et al., Arzeneim-Forsch, 26:1076-1078, 1976; Wright et al., Clin. Endocrinol., 24:375-382, 1986; Paccotti et al., Chronobiologica, 15:279-288, 1988; Valcavi et al., Clin. Endocrinol., 39:139-199, 1993). Melatonin may serve to reduce prostate enlargement (see above-cited U.S. and EP patents of Zisapel). Orally administered melatonin to castrated juvenile rats inhibited the androgen-dependent growth of the ventral prostate and the seminal vesicles (Gilad et al., J. of Urol., 159:1069-73, 1998). Recently, we have demonstrated high affinity melatonin receptors in the human benign prostate epithelial cells, which may affect cell growth and viability (Endocrinology, 137:1412-17, 1996).

In addition to the pineal gland, the eye also synthesizes melatonin. Recently melatonin has been implicated in the control of intraocular pressure and may be of use in glaucoma (Samples et al., Curr. Eye Res., 7:649-653, 1988; Rhode et al., Ophthalmic. Res., 25:10-15, 1993).

The kidney also expresses melatonin receptors, and melatonin has been shown to affect vasopressin and urine excretion (Song et al., FASEB J. 11:93-100, 1997; Yasin et al., Brain Res. Bull; 39:1-5, 1997).

It is clear that there exists a broad range of therapeutic uses for melatonin. Accordingly it is of continuing interest to identify novel compounds that interact with melatoninergic systems as potential therapeutic agents. These compounds may offer longer duration, selective localization and greater efficacy to those of melatonin.

Novel compounds related to melatonin, but with pharmacological or pharmacokinetic profiles different from melatonin, are likely to be important new pharmaceuticals. For examples, see U.S. Pat. No. 5,403,851 which discloses the use of substituted tryptamines, phenylalkylamines and related compounds, in order to treat a number of pharmaceutical indications including sleep disorders, endocrine indications, immune-system disorders etc. PCT Patent Application No. WO 87/00432 describes compositions, for treating or preventing psoriasis, which contain melatonin or related compounds. European Patent Application No. 0330625A2 discloses the production of melatonin and analogs thereof, for various therapeutic purposes, including the administration of melatonin in combination with an azidothymidine for the treatment of AIDS. Melatonin analogs based on the bioisosteric properties naphthalenic ring and the indole ring have been disclosed in J. Med. Chem., 1992, 35:1484-1485; EP 662471 A2 950712 of Depreux et al.; WO 9529173 A1 951102 of Ladlow et al.; U.S. Pat. No. 5,151,446 of Horn et al.; U.S. Pat. No. 5,194,614 of Adrieux et al. and U.S. Pat. No. 5,276,051 of Lesieur et al.

There is evidence suggesting both melatonin agonists and antagonists would be of potential therapeutic use for a variety of maladies and conditions. The present invention addresses the need for more therapeutically selective compounds than melatonin.

The entire contents of the above-cited patents, patent applications and literature articles are deemed to be incorporated herein by reference.

SUMMARY OF THE INVENTION

In one aspect, the present provides compounds having the formulae (I) and (II):

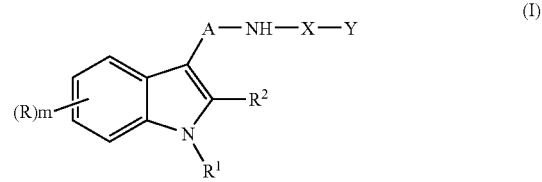

-continued

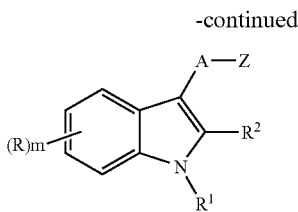

(II)

and their acid addition salts where the compounds are basic, wherein:

each R is independently selected from among halogen, $C_{1-4}$ alkyl, $C_{1-4}$ alkoxy, NR'R'', nitro, aryl, aryl-$C_{1-4}$ alkyl, or aryl-$C_{1-4}$ alkoxy, and each of R' and R'' is independently H or $C_{1-4}$ alkyl, or R'=R''=ClCH$_2$CH$_2$, or NR'R'' constitutes a saturated heterocyclic ring containing 3-8 ring members, and m is 0-4;

$R^1$ is selected from hydrogen, $C_{1-4}$ alkyl, $C_{1-4}$ alkanoyl, aryl-$C_{1-4}$-alkanoyl or aryl-$C_{1-4}$-alkyl; $R^2$ is selected from hydrogen, halogen, $C_{1-4}$ alkyl, $C_{1-4}$ alkoxy, aryl, aryl-$C_{1-4}$ alkyl, aryl-$C_{1-4}$ alkoxy and NR'R'' as defined above;

A is $C_{1-4}$ alkylene;

X is >CH$_2$, >C=O or >C=S;

Y is 2-furyl, 2-dihydrofuryl, 2-tetrahydrofuryl or (2-R°—COO—)phenyl, any of which may be substituted by 1-2 substituents selected from $C_{1-4}$ alkyl, $C_{1-4}$ alkoxy, OH, NR'R'' as defined above or nitro, or Y is styryl which may be ring-substituted by up to two substituents independently selected from among halogen, $C_{1-4}$ alkyl, $C_{1-4}$ alkoxy, OH, NR'R'' as defined above, nitro, aryl, aryl-$C_{1-4}$ alkyl, or aryl-$C_{1-4}$ alkoxy;

R° is $C_{1-4}$alkyl or NR'R'' as defined above;

Z is selected from 2-(p-(3,5-dioxoisoxazolidin-4-ylmethyl)phenoxy) ethylamino, p-(3,5-dioxoisoxazolidin-4-yl-methyl)phenoxy, 2-(p-(2,4-dioxothiazolidin-5-ylmethyl)phenoxy)ethylamino, p-(2,4-dioxothiazolidin-5-ylmethyl)phenoxy, 2-(p-(3,5-dioxoisoxazolidin-4-ylidenemethyl)phenoxy)ethylamino, p-(3,5-dioxoisoxazolidin-4-ylidenemethyl)phenoxy, 2-(p-(2,4-dioxothiazolidin-5-ylidenemethyl)phenoxy)ethylamino, p-(2,4-dioxothiazolidin-5-ylidenemethyl)phenoxy, 3,5-dioxoisoxazolidin-4-ylmethylamino, 2,4-dioxothiazolidin-5-ylmethylamino and cinnamoyloxy which may be ring-substituted by up to two substituents independently selected from among halogen, $C_{1-4}$ alkyl, $C_{1-4}$ alkoxy, OH, NR'R'' as defined above, nitro, aryl, aryl-$C_{1-4}$ alkyl, or aryl-$C_{1-4}$ alkoxy; and each aryl is phenyl which is unsubstituted or is substituted by 1-3 substituents selected from halogen, $C_{1-4}$ alkyl and $C_{1-4}$ alkoxy.

In particular embodiments of the invention, Y may be styryl, optionally ring-substituted by up to two substituents independently selected from among halogen, $C_{1-4}$ alkyl, $C_{1-4}$ alkoxy, OH, NR'R'' as defined above, nitro, aryl, aryl-$C_{1-4}$ alkyl, or aryl-$C_{1-4}$ alkoxy; and/or Z may be cinnamoyloxy, optionally ring-substituted by up to two substituents independently selected from among halogen, $C_{1-4}$ alkyl, $C_{1-4}$ alkoxy, OH, NR'R'' as defined above, nitro, aryl, aryl-$C_{1-4}$ alkyl, or aryl-$C_{1-4}$ alkoxy.

In another aspect, the invention provides a pharmaceutical formulation which comprises at least one pharmaceutically acceptable diluent, preservative, solubilizer, emulsifier, adjuvant, and/or carrier, and at least one member of the group consisting of the compounds of the invention as defined above and pharmaceutically acceptable salts thereof.

In yet another aspect, the invention provides use of at least one member of the group consisting of the compounds of the invention as defined above and pharmaceutically acceptable salts thereof, in the manufacture of a medicament for use in animal breeding, or for the prevention or treatment of prostate conditions, impotence, cardiovascular disorders, central nervous system and psychiatric disorders, chronobiological-based disorders, endocrine indications, neoplastic conditions, immune system, conditions associated with senescence, ophthalmological diseases, cluster headache, migraine and dermatological diseases.

DETAILED DESCRIPTION OF THE INVENTION

Without prejudice to the generality of the compounds of the present invention, a sub-group of presently preferred compounds is defined by the facts that in formula (I), m is 1 and R is a substituent in the 5-position of the indole ring. Another subgroup of the present compounds is defined by the facts that in formula (I), at least one of the following conditions applies, namely: m is 1 and R is 5-methoxy; and/or A is CH$_2$CH$_2$, and within this sub-group, illustrative embodiments of the compounds of the invention, particularly where $R^1$=$R^2$=H, are the following:

X is —CO— and Y is 2-furyl; or X is —CO— and Y is 2-tetrahydrofuryl; or

X is —CH$_2$— and Y is 2-tetrahydrofuryl; or X is —CO— and Y is 2-acetoxyphenyl; or X is —CO— and Y is 3,4-dihydroxystyryl; or Z is 3,4-dihydroxycinnamoyloxy.

The pharmaceutical formulation according to the invention is preferably characterized by at least one of the following features:

(i) it is adapted for oral, rectal, parenteral, transbuccal, intrapulmonary (e.g. by inhalaton) or transdermal administration;

(ii) it is in unit dosage form, each unit dosage comprising an amount of said at least one member which lies within the range of 0.0025-1000 mg;

(iii) it is a controlled release formulation, wherein said at least one member is released at a predetermined controlled rate.

In the pharmaceutical formulations of the present invention, the pharmaceutically acceptable diluents, preservatives, solubilizers, emulsifiers, adjuvants and carriers are those conventionally used in pharmaceutical and veterinary formulations. The present pharmaceutical formulations may be adapted for administration to humans and/or animals.

For oral administration, the pharmaceutical formulations may be utilized as e.g tablets, capsules, emulsions, solutions, syrups or suspensions. For parenteral administration, the formulations may be utilized as ampoules, or otherwise as suspensions, solutions or emulsions in aqueous or oily vehicles. The need for suspending, stabilizing and/or dispersing agents will of course take account of the fact of the solubility or otherwise of the active compounds, in the vehicles which are used in particular embodiments. The formulations may additionally contain e.g. physiologically compatible preservatives and antioxidants.

The pharmaceutical formulations may also be utilized as suppositories with conventional suppository bases such as cocoa butter or other glycerides. Alternatively, the formulations may be made available in a depot form which will release the active composition slowly in the body, over a preselected time period.

The compounds of the invention may further be administered by using transbuccal, intrapulmonary or transdermal delivery systems.

By way of further elaboration or explanation of conditions which it is presently contemplated may be amenable to treatment by administration of the present compounds, such conditions include benign and tumor prostate growth, and impotence; cardiovascular disorders including hypertension, preventing blood coagulation and protection from ischemic strokes; central nervous system and psychiatric disorders, e.g., sleep disorders, epilepsy and other convulsive disorders, anxiety, psychiatric diseases, neuropathy; neurodegenerative diseases e.g. Alzheimer's disease, Parkinson's disease, fever and analgesia; chronobiological-based disorders, e.g., jet lag, circadian sleep disorders such as delayed sleep syndrome, shift-work problems, and seasonal-elated disorders e.g. seasonal affective disorder (SAD); endocrine indications, e.g., contraception and infertility, precocious puberty, premenstrual syndrome, hyperprolactinemia, and growth hormone deficiency; anti-inflammatory indications e.g. rheumatoid arthritis; neoplastic diseases including e.g. cancer and other proliferative diseases; immune system disorders including AIDS; conditions associated with senescence; ophthalmological diseases; allergy diseases e.g. asthma; cluster headache, migraine; anti-Tardive Dyskensia effects, diabetes stabilization and weight gain disorders (leptin, obesity); and as an aid to animal breeding, e.g., regulation of fertility, puberty, pelage color.

It is still further contemplated that the present compounds (and particularly those where in formula (I) Y is optionally substituted styryl as defined above, and in formula (II) Z is optionally substituted cinnamoyloxy) may be of potential utility by virtue of having antioxidant and radical scavenging activity and the invention thus includes skin-protective and cosmetic compositions for topical application, such as (merely by way of illustrative examples) ointments, creams, salves and lotions, which comprise at least one compound according to the present invention, together with at least one diluent, carrier and adjuvant.

The invention will be illustrated by the following Examples.

EXAMPLE 1

5-Methoxy-3-(2-(tetrahydro-2-furamido)ethyl)indole (MLP-79)

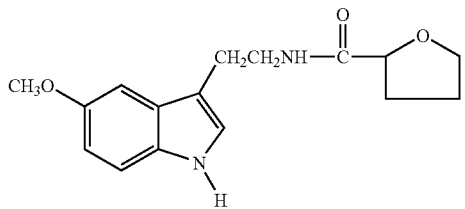

5-Methoxytryptamine (540 mg, 2.84 mmole) was suspended in benzene (5 ml). The mixture was cooled in an ice bath and a solution of tetrahydro-2-furoyl chloride (390 μl, 3.7 mmole) in benzene (5 ml) was slowly added. The reaction mixture was stirred at room temperature for 15 hours and was diluted with ether (25 ml). It was extracted with water (25 ml), NaHCO$_3$ solution (2×25 ml) and saturated NaCl solution (25 ml) dried (MgSO$_4$) and the solvent was removed in vacuo. Further purification was obtained by column chromatography on silica gel. The solvent was 50% ethyl acetate in CH$_2$Cl$_2$. Fractions of 10 ml were collected and the product was eluted in fractions 19-32. The product was obtained as an oil. The yield was 220 mg (~30%).

NMR (CDCl$_3$): δ=1.71-22.8 (m, 4H, CH$_2$CH$_2$); 2.94 (t, J=6.8 Hz, 2H, CH$_2$CH$_2$); 3.59 (q, J=6.8 Hz, 2H, CH$_2$NH); 3.70-3.82 (m, 2H, CH$_2$O); 3.81 (s, 3H, OCH$_3$); 4.32 (dd, J1=8.3 Hz, J2=5.8 Hz, 1H, C=OCHO); 6.75 (wide s, 1H, CH$_2$NH); 6.85 (dd, J1=8.75 Hz, J2=2.45 Hz, 1H, aromatic H); 7.05 (s, 1H C=CH); 7.10 (dd, J1=3.45 Hz, J2=0.72 Hz, 1H, aromatic H); 7.26 (d, J1=8.75 z, 1H, aromatic H); 8.17 (s, 1 H, NH). IR (neat): ν=3395 (NH), 3302 (NH), 2936, 2868, 1651, (CO amide), 1532 (CH=CH), 1484, 1215, 1066.

EXAMPLE 2

5-Methoxy-3-(2-(2-furamido)ethyl)indole (MLP-76)

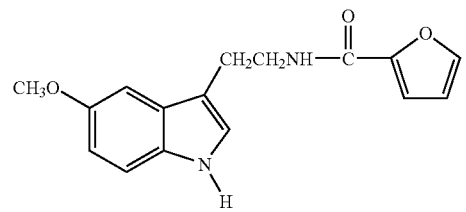

5-methoxytryptamine (300 mg, 1.57 mmole) was suspended in benzene (5 ml). The mixture was cooled in an ice bath and a solution of 2-furoyl chloride (190 μl, 1.9 mmole) in benzene (5 ml) was slowly added. The reaction mixture was stirred at room temperature for 15 hours and was diluted with ether (25 ml). It was extracted with water (25 ml), NaHCO$_3$ solution (2×25 ml) and saturated NaCl solution (25 ml) dried (MgSO$_4$) and the solvent was removed in vacuo. Further purification was obtained by column chromatography on silica gel. The solvent was 50% ethyl acetate in CH$_2$Cl$_2$. Fractions of 10 ml were collected and the product was eluted in fractions 10-18. The product was obtained as an oil which was crystallized from CH$_2$Cl$_2$ (0.5 ml) at −8° C. The yield was 220 mg (50%) m.p. 89-90° C.

NMR: (CDCl$_3$): δ=3.03 (t, J=675 Hz, 2H, CH$_2$CH$_2$); 3.75 (q, J=6.2 Hz, 2H, CH$_2$NH); 3.81 (s, 3H, OCH$_3$); 6.52 (wide s, 1H, CH$_2$NH); 6.46 (dd, J1=3.46 Hz, J2=1.75 Hz, 1H, CH=CH—CH); 6.86 (dd, J1=8.75 Hz, J2=2.45 Hz, 1H, aromatic H); 7.04 (d, J=1.76 Hz, 1H, CH=CH—CH); 7.05 (s, 1H, C=CH); 7.10 (dd, J1=3.45 Hz, J2=0.72 Hz, 1H, aromatic H); 7.26 (d, J1=8.75 z, 1H, aromatic H); 8.17 (s, 1H, NH). IR (KBr): ν=3361 (NH), 3260 (NH), 1630 (CO amide), 1594 (CH=CHO), 1535, (CH=CHO), 1295, 1211.

EXAMPLE 3

5Methoxy-3-(2-(tetrahydro-2-furylmethylamino) ethyl)indole (MLP-92)

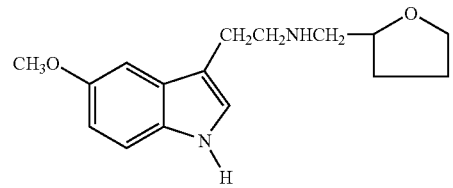

Tetrahydro-2-furoyl chloride (0.56 g, 4.2 mmole) in dry THF was added in dropwise manner to a stirred solution of 5-methoxytryptamine.HCl (90.94 g, 4.15 mole) and triethylamine (1.2 ml, 8.2 mmole) in THF (10 ml). The solution was stirred at room temperature for 20 hours. Ethyl acetate (25 ml) was added and the solution was washed with water, with 5% HCl, with 5% NaHCO$_3$, with water and saturated NaCl solution. It was dried over MgSO$_4$ and the solvent was removed under reduced pressure. The residue (0.3 g, 30% yield) was identified as the amide. A solution of the amide (0.285 g, 0.99 mmole) in dry THF (10 ml) was added in a dropwise fashion to a stirred suspension of LiAlH$_4$ (94 mg) in dry THF (10 ml) under atmosphere of argon. The reaction mixture was heated at reflux for 18 hours and cooled to 0° C. Water (1 ml) was added; the insoluble salts were removed by filtration and washed with ether (3×10 ml). The organic portions were washed with sutured NaCl solution (20 ml) and the solvent was dried (MgSO$_4$) and removed. The residue (0.178 g, 65% yield) was purified by flash chromatography using silica gel (eluted with CH$_2$Cl$_2$: CH$_3$OH 92:8 containing about 0.03% NH$_3$). Fractions of 10 ml were collected and the product was eluted from fractions 11-18. It was obtained as a light yellow oil.

NMR: (CDCl$_3$): δ=1.45-2.23 (m, 4H, CH$_2$CH$_2$O); 1.75 (ws*, 2H, 2NH$_2$); 2.65-2.85 (m, 2H, CH$_2$NH); 2.99 (s, 4H, CH$_2$CH$_2$NH); 3.70-3.86 (m, 2H, CH2O—); 3.86 (s, 3H, OCH$_3$); 3.88-4.16(m, 1H, CHO—); 6.85 (dd**, J1=875 Hz, J2=2.45 Hz, 1H, aromatic H); 7.05 (s, 1H, C=CH); 7.05 (dd, J1=4.85 Hz, J2=2.45 Hz, 1H, aromatic H); 7.26 (d, J=11.25 Hz, 1H, aromatic H); 7.98 (s, 1H, NH). Addition of trifuroacetic acid changed the spectrum in a manner expected for the transformation of the free amines to ammonium derivatives. The major changes were the disappearance of the amino peaks at 1.75 and 7.98.

IR (neat): ν=3397 (NH), 3292 (NH), 2936, 2828, 1624, (CH=CH), 1585, 1486, 1455, 1441, 1215, 1066.

ws*=wide singlet; dd**=doublet of doublets.

EXAMPLE 4

5-Methoxy-3-(2-2-acetoxybenzamido)ethyl)indole (MLP-77)

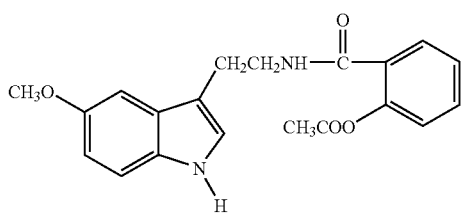

5-Methoxytryptamine (400 mg, 2.1 mmole) was suspended in benzene (5 ml). The mixture was cooled in an ice bath and a solution of acetylsalicyloyl chloride (500 mg, 2.5 mmole) in benzene (5 ml) was slowly added. The reaction mixture was stirred at room temperature for 15 hours and was diluted with ether (25 ml). It was extracted with water (25 ml), NaHCO$_3$ solution (2×25 ml) and saturated NaCl solution (25 ml), dried (MgSO$_4$) and the solvent was removed in vacua. Further purification was obtained by column chromatography on silica gel. The solvent was ethyl acetate:CH$_2$Cl$_2$ (4:5). Fractions of 10 ml were collected and the product was eluted in fractions 7-10. The product was obtained as an oil which was crystallized from CH$_2$Cl$_2$ (0.5 ml) at –8° C. The yield was 270 mg (40%). M.P=120-121° C.

NMR: (CDCl$_3$): δ=1.95 (s, 3H, CH$_3$CO); 3.03 (t, J=6.6 Hz, 2H, CH$_2$CH$_2$); 3.79 (q, J=5.6 Hz, 2H, CH$_2$NH); 3.81 (s, 3H, OCH$_3$); 6.42 (wide s, 1H, CH$_2$NH); 6.86 (dd, J1=8.75 Hz, J2=2.45 Hz, 1H, aromatic H); 7.05 (s, 1H C=CH); 7.04 (d, J1=8.75 z, 1H, aromatic H); 7.29-7.23 (m, 2H, aromatic H); 7.71 (td*, J1=8.75 Hz, J1=8.75 Hz, J2=2.45 Hz, J3=1.25 Hz, 1H, aromatic H); 7.43 (dd, J1=9 Hz, J2=6.5 Hz, aromatic H); 8.05 (s, 1H, NH). IR (KBr): ν=3421(NH), 3344 (NH), 1745, (C=O ester), 1642 (C=O amide), 1530, (CH=CH), 1485, 1218.

dd=doublet of doublets; td*=doublet of triplets.

EXAMPLE 5

Caffeic Acid 5-Methoxytryptamide

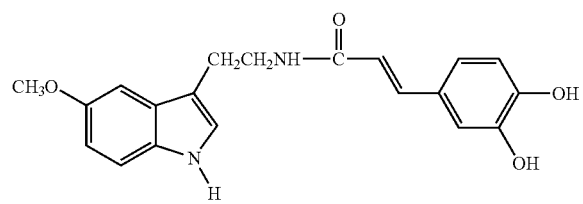

3,4-Dihydroxycinnamic acid (1.13 g, 6.27 mmole) was dissolved in thionyl chloride (25 ml) and the solution was stirred for 5 hours at 40-60° C. The solvent was removed, the residue was dissolved in thoroughly dried ethyl acetate and the solution was slowly added to a solution of 5-methoxy tryptamine (1.2 g) in benzene, which contained also ethylamine (1 ml). The mixture was stirred overnight, water (10 ml) was added and the mixture again stirred for 15 minutes. The solvents were removed, the residue was dissolved in ethyl acetate and the solution was washed successively with water, saturated NaHCO$_3$ solution, water and brine, and then dried over Na$_2$SO$_4$. The solvent was removed and the product was purified by column chromatography using 1:9 methanol/dichloromethane. The purification process was repeated three times to remove byproducts. The fraction identified as the caffeic acid 5-methoxytryptamide was further purified by recrystallization from ethyl acetate/hexane solution. The compound was obtained as white crystals (yield about 60%).

NMR (CD$_3$OD): d=2.85 (t, 2H, J=7.25 Hz, CH$_2$NH); 3.43 (t, 2H, J=7.25 Hz, CH$_2$CH$_2$NH); 3.69 (s, 3H, OCH3); 6.23 (d, 1H, J=15.5 Hz, =CHCONH); 6.64 (dd, J1=11.25 HZ, J2=2.5 Hz, 1H, aromatic H, caffeic); 6.63 (dd, J1=8.75 Hz, J2=2.5 Hz, 1H, aromatic H tryptyl); 6.78 (dd, J1=8.75 Hz, J2=2.5 Hz, 1H, aromatic H, tryptyl c); 6.95 (s, 1H—N—C=CH); 6.92 (dd, J1=19.5 Hz, J2=2.45 Hz, 1H, aromatic H, caffeic); 7.10 (d, J=7 Hz, 1H, aromatic H, caffeic); 7.28 (d, J=15.5 Hz, 1H, CH=CH). The proton of the OH and NH groups could not be seen since the spectrum was taken in methanol, where these protons exchange with the deuterium of the solvent.

Radical scavenging activity was assayed in duplicates according to Blois, M. S., Nature, 1958, 181:1199. The reaction mixture contained 3 ml of 0.1 mM DPPH (in 95% ethanol) and 0.5 ml of the test compound. After 20 min. incubation at room temperature A$_{517}$ was determined. The scavenging activity was measured as the decrease in A$_{517}$ of the DPPH radical expressed as a percentage of the control value. Results are shown in the following Table.

TABLE 1

Scavenging activity on DPPH radicals (antioxidant effect)

| Addition (10 µM) | Relative ratio of scavenging activity compared with Vitamin E (tocopherol) |
|---|---|
| Vitamin E (tocopherol) | 1 |
| Caffeic acid | 2.8 |
| caffeic acid 5-methoxytryptamide | 3.2 |
| Vitamin C (ascorbic acid) | 1 |
| Melatonin | 0.25 |

EXAMPLE 6

Caffeic Acid 5-Methoxyltryptophol Ester

This is prepared analogously to Example 5, substituting the equivalent quantity of 5-methoxytryptophol for 5-methoxytryptamine The product has the structure:

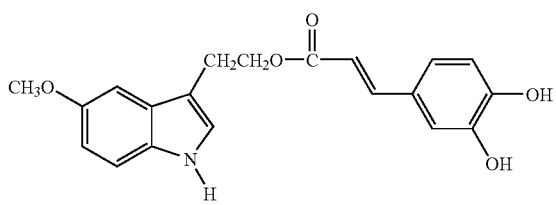

EXAMPLE 7

2-(p-(2,4-dioxothiazolidin-5-ylmethyl)phenoxy) ethyl-5-methoxyindole

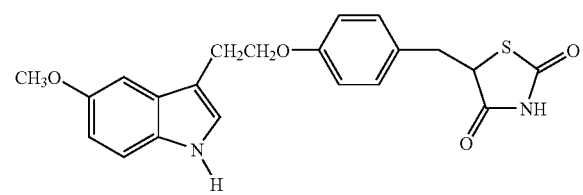

(a) Preparation of Starting Material

In a suitably equipped flask, there were dissolved 25 g (0.131 mole) 5-methoxytryptophol in 300 ml dimethylacetamide (DMA), and to this solution were added 17.1 g (0.138 mole) p-fluorobenzaldehyde and 36.2 g potassium carbonate, and a further 120 ml DMA. The mixture was stirred for 30 minutes at room temperature, and then at 100° C. for 264 hours. The mixture was then cooled, poured into 500 ml water and stirred vigorously for about one hour, when a light-yellow solid formed. The suspension was extracted with a total of about 2.5 l ethyl acetate, adding some NaCl to the aqueous layer as an aid to separation. The combined organic layer is dried with sodium sulfate and concentrated in vacuo to give about 110 g of dark-brown liquid still containing some DMA. The liquid is dissolved in 500 ml toluene, filtered and 500 ml water is added to the filtrate and stirred. A few drops of 20% NaOH are added to give an alkaline pH, then NaCl is added to prevent the formation of an emulsion. After stirring for one hour, the organic layer is separated. The extraction with toluene is repeated twice. The combined organic layers are evaporated to dryness in vacuo to give 30 g of a brown oil, which is purified by chromatography on 500 g silica gel, using the following gradient of eluent: 1 1 chloroform; 1 1 95:5 chloroform/acetone; 3 1 90:10 chloroform/acetone; 500 ml 84:16 chloroform/acetone; 1 1 80:20 chloroform/acetone; 200 ml 50:50 chloroform/acetone; 300 ml 40:60 chloroform/acetone. The combined fractions containing 3-2p-formylphenoxyethyl)-5-methoxyindole (TLC: 90:10 chloroform/acetone Rf=0.21; yellow spot) are evaporated in vacuo to give 12.3 g of a brown oil, which is used in the next step.

(b) Preparation of Intermediate

To 12.3 g (0.0417 mole) of the product of step (a) dissolved in 500 ml toluene, in a suitably equipped flask, there were added 8.4 g (0.0717 mole) 2,4-thiazolidinedione, and the mixture was stirred for 30 minutes, adding 50 ml toluene to aid dissolution. Piperidine (5.2 ml) was added, the temperate was raised 110° C. and the mixture stirred at this temperature for about three hours. After cooling, a yellow solid precipitated; this was filtered off, washed with ethyl acetate and dried to give as a yellow solid 11 g of 2-(p-(2,4-dioxothiazolidin-5-ylidenemethyl)phenoxy)ethyl-5-methoxyindole of formula

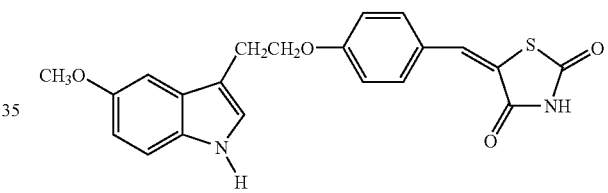

(c) 2-(p-(2,4-dioxothiazolidin-5-ylmethyl)phenoxy)ethyl-5-methoxyindole.

Under an argon atmosphere, 70 ml of 1,4-dioxane were refluxed in a suitably equipped flask, 1 g of the product of step (b) was added, to give a clear solution after about 30 minutes, which was cooled to 50° C., followed by addition of 70 ml methanol, this flask being kept at 50° C. In a second flask, there was placed under an argon atmosphere, 1 g Mg turnings covered with methanol; two crystals of iodine were added, and after foaming began the mixture was stirred until the iodine color disappeared. The contents of the first flask were then poured into the second flask, and the temperature raised to 64° C. A further 1.4 g Mg turnings were added over 4 hours, and the reaction mixture was allowed to reflux for 5 days, until conversion as determined by UV was >95%. The mixture was cooled and poured into 500 ml of 20% NH$_4$Cl solution extracted with 3×200 ml dichloromethane, washed with 5% aq. citric acid and water and rotoevaporated to give a solid which was dissolved in methanol and crystallized at −18° C. There were obtained 400 mg of the title compound as yellow crystals.

Biological Testing of Compounds of the Invention

Experiment 1

The effects of orally administered compounds of the invention, MLP-76,77, 79 and 92, on androgen-dependent prostatal regrowth in adult castrated male rats was investigated. Male rats (2.5 months old) were castrated under anesthesia and left to recover for 7 days. During this period, the average weight of the prostate decreased by approximately 75%. Beginning on day 7 after castration, the rats were given daily subcutaneous injections of either oil vehicle (control) or oil vehicle containing testosterone propionate (1 mg/kg body weight per day) for 4 days at 1 hour before lights off. One group of rats was divided into subgroups (3-4 per cage), each subgroup was given either a compound of the invention, melatonin (10 mg dissolved in 10 µl ethanol per liter of drinking water) or vehicle only (100 µl ethanol per liter of drinking water) through the drinking water. A second group of rats was divided into subgroups (3-4 per cage), each subgroup was given either MLP-92, melatonin (0.1 or 0.01 mg dissolved in 100 µl ethanol per liter of drinking water) or vehicle only (100 µl ethanol per liter of drinking water) through the drinking water. It was estimated that each rat in the sub-groups receiving a compound of the invention had an intake of approximately 4 ml solution, i.e. about 40 mcg derivative per day. In the morning following the last injection, the rats were sacrificed and the seminal vesicles and ventral prostates were removed and weighed.

The results are shown in Tables 2 and 3. Testosterone increased the weight of the seminal vesicles and ventral prostate in the castrated animals compared to untreated-controls. Melatonin and the four compounds of the invention decreased significantly the testosterone-mediated regrowth of the ventral prostate gland in the presence of testosterone (Table 2). MLP-92 and MLP-76 were more potent then MLP-79, MLP-77 and melatonin. The effects of both melatonin and MLP-92 on the prostate re-growth were dose-dependent, whereas melatonin was less effective than the inventive compound (IC50=88 nM, 230 nM, for MLP-92 and melatonin respectively).

This experiment indicates a direct inhibitory action of orally administered compounds of the invention on prostatal growth in adult rats, which resemble the effect of melatonin.

TABLE 2

Effects of testosterone and compounds of the invention on ventral prostate and seminal vesicles weight of castrated rats

| (10 mg/l drinking water) | Prostate (mg/g body weight) | A | Seminal Vesicles (mg/g body weight) | B |
|---|---|---|---|---|
| Control (n = 3) | 0.27 ± 0.07 | | 0.73 ± 0.05 | |
| Testosterone (n = 4) | 0.77 ± 0.02 | | 2.38 ± 0.16 | |
| Testosterone + MLP-92 (n = 4) | 0.49 ± 0.04 | 66 | 1.54 ± 0.21 | 51 |
| Testosterone + MLP-77 (n= 4) | 0.57 ± 0.05 | 40 | 2.69 ± 0.49 | −18 |
| Testosterone + MLP-76 (n = 4) | 0.49 ± 0.09 | 66 | 1.82 ± 0.25 | 44 |
| Testosterone + MLP-79 (n = 3) | 0.50 ± 0.04 | 54 | 2.00 ± 0.39 | 23 |
| Testosterone + Melatonin (n = 3) | 0.55 ± 0.08 | 44 | 1.88 ± 0.03 | 30 |

A = % inhibition of testosterone-stimulated growth (prostate)
B = % inhibition of testosterone-stimulated growth (seminal vesicles)

TABLE 3

Effects of testosterone and different doses of MLP-92 on ventral prostate and seminal vesicles weight of castrated rats

| | Prostate (mg/g body weight) | A | Seminal Vesicles (mg/g body weight) | B |
|---|---|---|---|---|
| Control (n = 4) | 0.36 ± 0.11 | | 0.59 ± 0.03 | |
| Testosterone | 0.62 ± 0.1 | | 1.95 ± 0.24 | |
| Testosterone (n = 3) + MLP-92 0.01 mg/l | 0.57 ± 0.04 | 19 | 1.57 ± 0.25 | 28 |
| Testosterone (n = 3) + MLP-92 0.1 mg/l | 0.46 ± 0.1 | 62 | 1.45 ± 0.13 | 37 |
| Testosterone (n = 3) + Melatonin 0.01 mg/l | 0.66 ± 0.08 | −15 | 1.81 ± 0.28 | 10 |
| Testosterone (n = 3) + Melatonin 0.1 mg/l | 0.54 ± 0.09 | 31 | 1.55 ± 0.24 | 30 |

A = % inhibition of testosterone-stimulated growth (prostate)
B = % inhibition of testosterone-stimulated growth (seminal vesicles)

Experiment 2

The distribution of MLP-92 and MLP-77 in various organs of the rat was examined. 100 mcl saline containing $1 \times 10^6$ dpm $^{125}$I-labelled compounds of the invention (labelling as described by Vakkuri et al., Acta Endocrinol., 106, 152-7, 1984) were injected (ip) to adult male rats. The rats were sacrificed 1 h after injection and various organs were dissected out and weighted. The contents of the radioactive derivatives in the rat organs (Brain, Hypothalamus, Pituitary, Eyes, Thyroid, Heart, Lungs, Kidneys, Spleen, Testis, Prostate and seminal vesicle) were determined using a gamma-counter and the results are presented as dpm/g organ wet-weight. For comparison, the results of a similar experiment (Withyachumnarnkul et al., Life Sci., 38: 1757-65, 1986) using $^3$H-melatonin are also shown (Table 4).

The results demonstrate selective accumulation of MLP-92, 79 and 77 in the prostate compared to the high accumulation of melatonin in the pituitary. These retention patterns raise the possibility that the present compounds could be of potential therapeutic use for the treatment of benign and tumor prostate growth.

TABLE 4

The distribution of $^{125}$I labelled MLP-92 and 125-I MLP-77 in the adult rat male body 1 h post IP injection of $6 \times 10^6$ dpm.

| | $^3$H-Melatonin dpm × 10$^3$/100 g wet tissue | $^{125}$I-MLP-92 dpm × 1000/ g wet tissue | $^{125}$I-MLP-77 dpm × 1000/ g wet tissue | $^{125}$I-MLP-79 dpm × 1000/ g wet tissue |
|---|---|---|---|---|
| Hypothalamus | 0.6 | 1.02 | 3.3 | 0.6 |
| Brain stem | | 23 | 1.51 | 0.43 |
| Forebrain | | 0.33 | 0.75 | 0.53 |
| Pituitary | 1.84 | 5 | 8.9 | 0.73 |
| Eye | | 1 | 6.7 | 1 |
| Thyroid | | 1.54 | 10.9 | 2.5 |
| Heart | | 1 | 7.42 | 1.66 |
| Lungs | 0.74 | 1.77 | 14.4 | 1.53 |
| Liver | | 1.57 | 9 | 1.46 |
| Spleen | | 1.2 | 10 | 1.43 |
| Kidney | | 2 | 15.3 | 2.46 |
| Testis | 0.6 | 1 | 8.9 | 1.4 |
| Prostate | 1.0 | 6.14 | 18 | 2.23 |
| Seminal Vesicles | 1.0 | 0.8 | 5.6 | 1 |

While the present invention has been particularly described with reference to certain embodiments, it will be apparent to those skilled in the art that many modifications and variations may be made. The invention is accordingly not to be construed as limited in any way by such embodiments, rather its concept is to be understood according to the spirit and scope of the claims which follow.

The invention claimed is:

1. A compound having the formula (I):

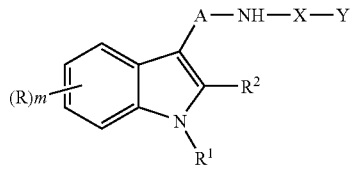

or an acid addition salt thereof where the compounds are basic, wherein:
each R is independently selected from among halogen, $C_{1-4}$ alkyl, $C_{1-4}$ alkoxy, NR'R", nitro, aryl, and aryl-$C_{1-4}$ alkoxy and each of R' and R" independently is H or $C_{1-4}$ alkyl, or R'=R"=ClCH$_2$CH$_2$, or NR'R" constitutes a saturated heterocyclic ring containing 3-8 ring members, and m is 1-4;
$R^1$ is hydrogen;
$R^2$ is selected from hydrogen, $C_{1-4}$ alkyl, $C_{1-4}$ alkoxy and NR'R" as defined above;
A is $C_{1-4}$ alkylene;
X is >CH$_2$, >C=O or >C=S; and
Y is 2-furyl, 2-dihydrofuryl or 2-tetrahydrofuryl, any of which may be substituted by 1-2 substituents selected from $C_{1-4}$ alkyl, $C_{1-4}$ alkoxy, OH, NR'R" as defined above or nitro.

2. A compound having the formula (I):

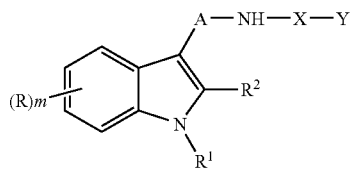

or an acid addition salt thereof where the compounds are basic, wherein:
each R is independently selected from among halogen, $C_{1-4}$ alkyl, $C_{1-4}$ alkoxy, NR'R", nitro, aryl, and aryl-$C_{1-4}$ alkoxy and each of R' and R" independently is H or $C_{1-4}$ alkyl, or R'=R"=ClCH$_2$CH$_2$, or NR'R" constitutes a saturated heterocyclic ring containing 3-8 ring members, and m is 1-4;
$R^1$ is hydrogen;
$R^2$ is selected from hydrogen, $C_{1-4}$ alkyl, $C_{1-4}$ alkoxy and NR'R" as defined above;
A is $C_{1-4}$ alkylene;
X is >CH$_2$, >C=O or >C=S;
Y is (2-$R^o$—COO—) phenyl, which may be substituted by 1-2 substituents selected from $C_{1-4}$ alkyl, $C_{1-4}$ alkoxy, OH, NR'R", as defined above or nitro; and
$R^o$ is $C_{1-4}$ alkyl or NR'R", as defined above;
wherein each aryl is phenyl which is unsubstituted or is substituted by 1-3 substituents selected from halogen, $C_{1-4}$ alkyl and $C_{1-4}$ alkoxy.

3. A compound having the formula (II):

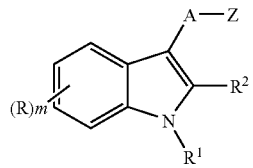

or an acid addition salt thereof where the compounds are basic, wherein:
each R is independently selected from among halogen, $C_{1-4}$ alkyl, $C_{1-4}$ alkoxy, NR'R", nitro, aryl, and aryl-$C_{1-4}$ alkoxy and each of R' and R" independently is H or $C_{1-4}$ alkyl, or R'=R"=ClCH$_2$CH$_2$, or NR'R" constitutes a saturated heterocyclic ring containing 3-8 ring members, and m is 0-4;
$R^1$ is hydrogen;
$R^2$ is selected from hydrogen, $C_{1-4}$ alkyl, $C_{1-4}$ alkoxy and NR'R" as defined above;
A is $C_{1-4}$ alkylene; and
Z is selected from 2-(p-(3,5-dioxoisoxazolidin-4-ylmethyl)phenoxy ethylamino, p-(3,5-dioxoisoxazolidin-4-ylmethyl)phenoxy, 2-(p-(2,4-dioxothiazolidin-5-ylmethyl)phenoxy)ethylamino, 2-(p-3,5-dioxoisoxazolidin-4-ylidenemethyl)phenoxy) ethylamino, p-(3,5-dioxoisoxazolidin-4-ylidenemethyl)phenoxy, 2-(p-2,4-dioxothiazolidin-5-ylidenemethyl)phenoxy)ethylamino, 3,5-dioxoisoxazolidin-4-ylmethylamino, 2,4-dioxothiazolidin-5-ylmethylamino and cinnamoyloxy which is ring-substituted by up to two substituents independently selected from among halogen, $C_{1-4}$ alkyl, $C_{1-4}$alkoxy, OH, NR'R" as defined above, nitro, aryl, aryl-$C_{1-4}$ alkyl, or aryl-$C_{1-4}$ alkoxy;
wherein each aryl is phenyl which is unsubstituted or is substituted by 1-3 substituents selected from halogen, $C_{1-4}$ alkyl and $C_{1-4}$ alkoxy.

4. A composition selected from skin-protective and cosmetic compositions for topical application, which comprises at least one compound according to claim 3 having activity selected from antioxidant and radical scavenging activity, together with at least one diluent, carrier and adjuvant.

5. A compound according to claim 3, wherein Z is selected from 2-(p-(3,5-dioxoisoxazolidin-4-ylmethyl)phenoxy) ethylamino, p-(3,5-dioxoisoxazolidin-4-ylmethyl)phenoxy, 3,5-dioxoisoxazolidin-4-ylmethylamino, 2-(p-(2,4-dioxothiazolidin-5-ylmethyl)phenoxy)ethylamino and 2,4-dioxothiazolidin-5-ylmethylamino.

6. A compound according to claim 1, 2 or 3, wherein m is 1 and R is a substituent in the 5-position of the indole ring.

7. A compound according to claim 1, 2 or 3, wherein at least one of the following conditions applies, namely: m is 1 and R is 5-methoxy; or A is CH$_2$CH$_2$.

8. A compound according to claim 1, which is 5-methoxy-3-(2-(2-furamido)ethyl)indole having the formula

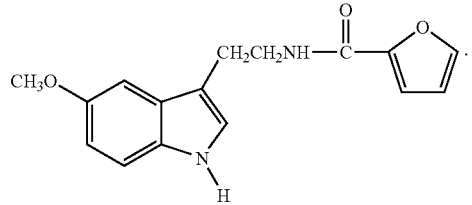

9. A compound according to claim 1, which is 5-methoxy-3-(2-(tetrahydro-2-furamido)ethyl)indole having the formula

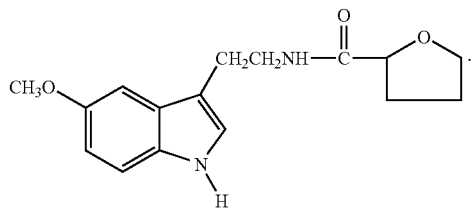

10. A compound according to claim 1, which is 5-methoxy-3-(2-(tetrahydro-2-furylmethylamino)ethyl)indole having the formula

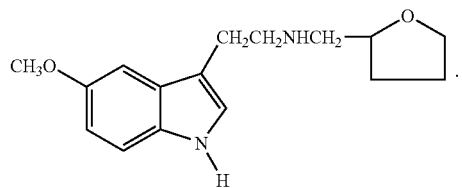

11. A compound according to claim 2, which is 5-methoxy-3-(2-(2-acetoxybenzamido)ethyl)indole having the formula

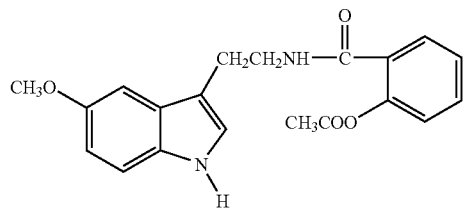

12. A pharmaceutical formulation which comprises at least one pharmaceutically acceptable diluent, preservative, solubilizer, emulsifier, adjuvant, or carrier, and at least one member of the group consisting of the compounds defined in claim 1, 2 or 3, and pharmaceutically acceptable salts thereof.

13. A pharmaceutical formulation according to claim 12, wherein said at least one member is selected from compounds having the formula (II)

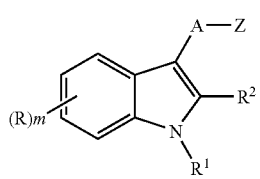

or an acid addition salt thereof where the compounds are basic, wherein:

each R is independently selected from among halogen, $C_{1-4}$ alkyl, $C_{1-4}$ alkoxy, NR'R", nitro, aryl, and aryl-$C_{1-4}$ alkoxy and each of R' and R" independently is H or $C_{1-4}$ alkyl, or R'=R"=ClCH$_2$CH$_2$, or NR'R" constitutes a saturated heterocyclic ring containing 3-8 ring members, and m is 0-4;

$R^1$ is hydrogen;

$R^2$ is selected from hydrogen, $C_{1-4}$ alkyl, $C_{1-4}$ alkoxy and NR'R" as defined above;

A is $C_{1-4}$ alkylene; and

Z is selected from 2-(p-(3,5-dioxoisoxazolidin-4-ylmethyl)phenoxy)ethylamino, p-(3,5-dioxoisoxazolidin-4-ylmethyl)phenoxy, 3,5-dioxoisoxazolidin-4-ylmethylamino, 2-(p-(2,4-dioxothiazolidin-5-ylmethyl)phenoxy)ethylamino and 2,4-dioxothiazolidin-5-ylmethylamino and pharmaceutically acceptable salts thereof.

14. A pharmaceutical formulation according to claim 12, which is characterized by at least one of the following features:
(i) it is adapted for oral, rectal, parenteral, transbuccal, intrapulmonary or transdermal administration;
(ii) it is in unit dosage form, each unit dosage comprising an amount of said at least one member which lies within the range of 0.0025-1000 mg; or
(iii) it is a controlled release formulation, wherein said at least one member is released at a predetermined controlled rate.

15. A pharmaceutical formulation according to claim 13, which is characterized by at least one of the following features:
(i) it is adapted for oral, rectal, parenteral, transbuccal, intrapulmonary or transdermal administration;
(ii) it is in unit dosage form, each unit dosage comprising an amount of said at least one member which lies within the range of 0.0025-1000 mg; or
(iii) it is a controlled release formulation, wherein said at least one member is released at a predetermined controlled rate.

16. A composition selected from skin-protective and cosmetic compositions for topical application, which comprises at least one compound according to claim 1 or 2 having activity selected from antioxidant and radical scavenging activity, together with at least one diluent, carrier and adjuvant.

17. A composition according to claim 4, in which in the compound of formula (II) Z is substituted cinnamoyloxy.

* * * * *